United States Patent [19]
Faries, Jr. et al.

[11] Patent Number: 6,035,855
[45] Date of Patent: Mar. 14, 2000

[54] SURGICAL DRAPE FOR USE WITH SURGICAL SLUSH MACHINES HAVING AN AUTOMATIC DISLODGEMENT MECHANISM

[75] Inventors: Durward I. Faries, Jr., McLean, Va.; Bruce R. Heymann, Silver Spring, Md.; Mark Licata, Richmond, Va.

[73] Assignee: O.R. Solutions, Inc., Chantilly, Va.

[21] Appl. No.: 08/810,104

[22] Filed: Feb. 25, 1997

[51] Int. Cl.$^7$ .................................................. A61B 19/00
[52] U.S. Cl. ............................................. 128/849; 62/66
[58] Field of Search .................................. 128/849–856; 62/66, 68, 340, 342; 4/DIG. 18

[56] References Cited

U.S. PATENT DOCUMENTS

| | | |
|---|---|---|
| 2,277,605 | 3/1942 | Palitzsch . |
| 2,778,921 | 1/1957 | Jepson . |
| 3,155,260 | 11/1964 | Widener . |
| 3,902,484 | 9/1975 | Winters . |
| 4,393,659 | 7/1983 | Keyes et al. . |
| 4,474,016 | 10/1984 | Winchell . |
| 4,522,041 | 6/1985 | Menzel . |
| 4,782,835 | 11/1988 | Bernardini . |
| 4,903,710 | 2/1990 | Jessamine ................................ 128/849 |
| 4,934,152 | 6/1990 | Templeton . |
| 4,967,061 | 10/1990 | Weber, Jr. et al. . |
| 5,040,699 | 8/1991 | Gangemi . |
| 5,042,455 | 8/1991 | Yue et al. . |
| 5,129,033 | 7/1992 | Ferrara et al. . |
| 5,163,299 | 11/1992 | Faries, Jr. et al. . |
| 5,174,306 | 12/1992 | Marshall . |
| 5,310,524 | 5/1994 | Campbell et al. . |
| 5,331,820 | 7/1994 | Faries, Jr. et al. . |
| 5,333,326 | 8/1994 | Faries, Jr. et al. . |
| 5,363,746 | 11/1994 | Gordon . |
| 5,374,813 | 12/1994 | Shipp . |
| 5,383,476 | 1/1995 | Peimer et al. . |
| 5,386,835 | 2/1995 | Elphick et al. . |
| 5,400,267 | 3/1995 | Denen et al. . |
| 5,400,616 | 3/1995 | Faries, Jr. et al. . |
| 5,402,644 | 4/1995 | Faries, Jr. et al. . |
| 5,429,801 | 7/1995 | Faries, Jr. et al. . |
| 5,435,322 | 7/1995 | Marshall . |
| 5,443,082 | 8/1995 | Mewburn . |
| 5,449,892 | 9/1995 | Yamada . |
| 5,457,962 | 10/1995 | Faries, Jr. et al. . |
| 5,463,213 | 10/1995 | Honda . |
| 5,502,980 | 4/1996 | Faries, Jr. et al. . |
| 5,522,095 | 6/1996 | Faries, Jr. et al. . |
| 5,524,643 | 6/1996 | Faries, Jr. et al. . |
| 5,539,185 | 7/1996 | Polster . |
| 5,551,240 | 9/1996 | Faries, Jr. et al. . |
| 5,615,423 | 4/1997 | Faries, Jr. et al. . |
| 5,653,938 | 8/1997 | Faries, Jr. et al. . |

*Primary Examiner*—Michael A. Brown

[57] ABSTRACT

A surgical drape for use in a thermal treatment system having an automatic dislodgement mechanism for dislodging congealed liquid is accomplished by a drape having either a coefficient of friction approximately in the range of 0.4–1.0 as measured against steel per ASTM 1983 a metalocine-based olefin film having a flexibility approximately in the range of 10K–12K psi secant modulus measured by ASTM D882, a securing mechanism, or a preformed container portion having ribs or ridges to prevent the drape from being drawn beneath the automatic dislodgement mechanism. The securing mechanisms may be attached to the drape either at the ends of a drape portion hanging down from a top surface of the system, or at a location coincident the top surface of the machine. Further, the securing mechanisms may be separate units disposed on the drape subsequent to disposal of the drape in the basin. The securing mechanisms ensure that there is only a sufficient amount of the drape portion disposed in the thermal treatment system basin to form a drape receptacle without leaving any margin for excess portions of the drape to be drawn beneath the dislodgement mechanism. Alternatively, the drape may include a preformed container portion having ribs disposed in the container portion walls to allow air beneath the container portion to prevent the container portion from being drawn by suction against the basin and beneath the dislodgement mechanism.

50 Claims, 6 Drawing Sheets

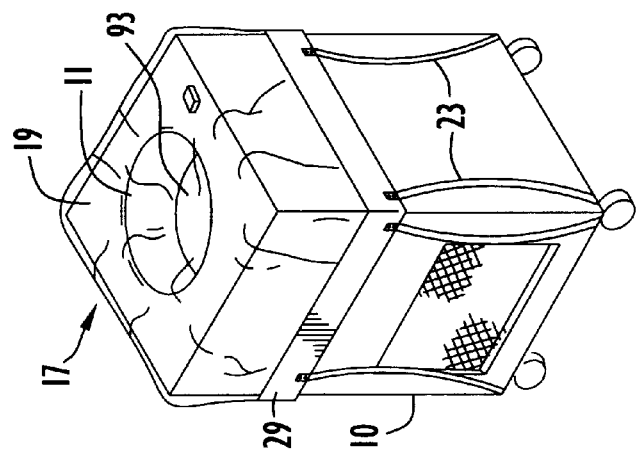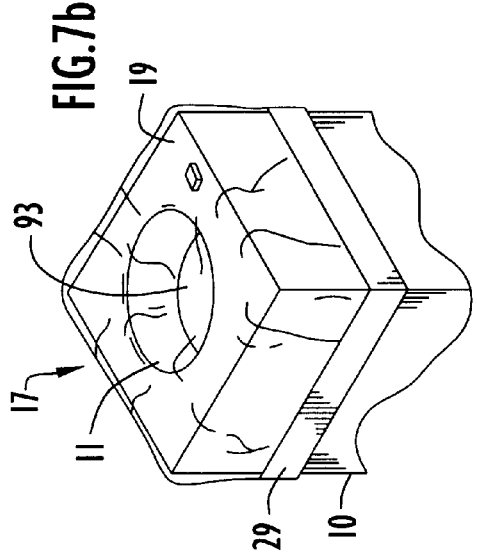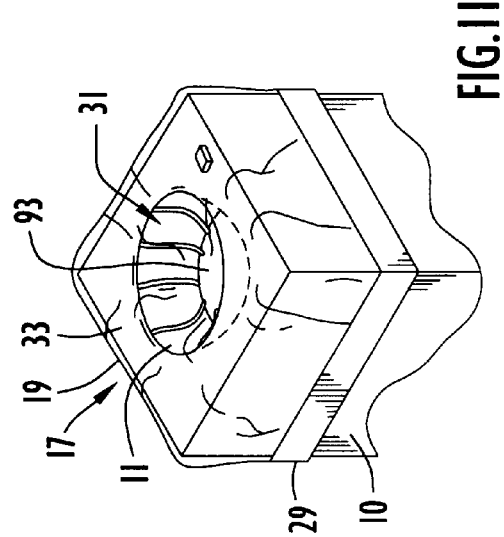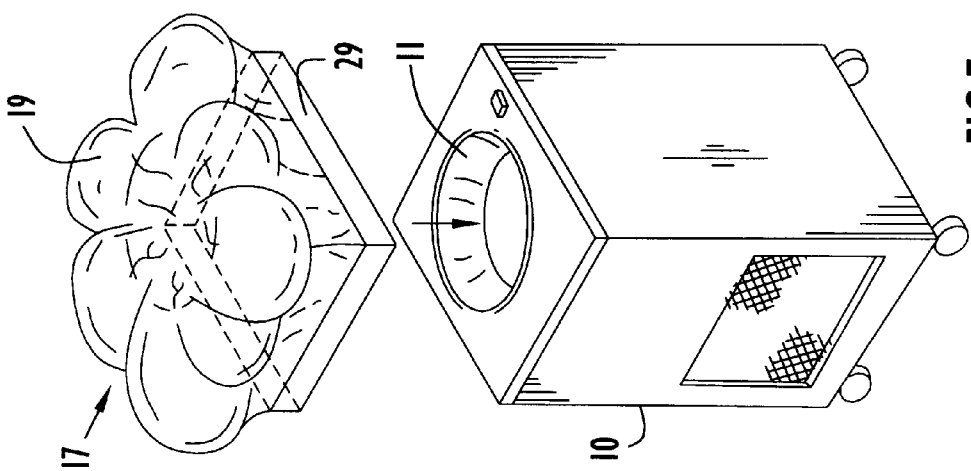

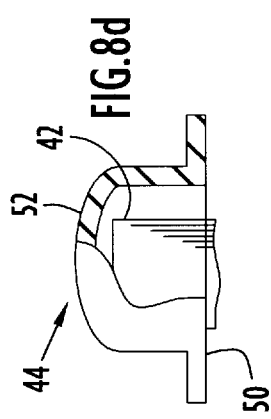
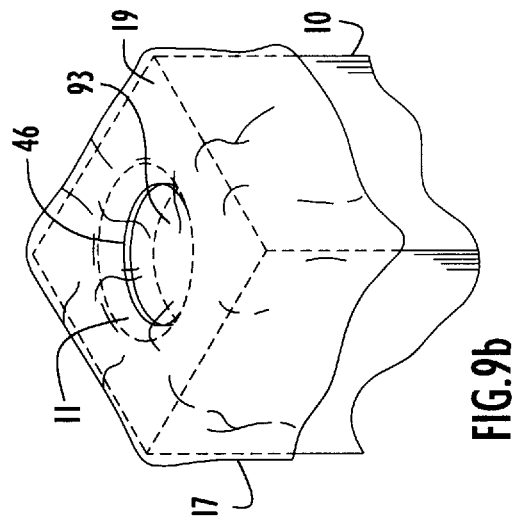
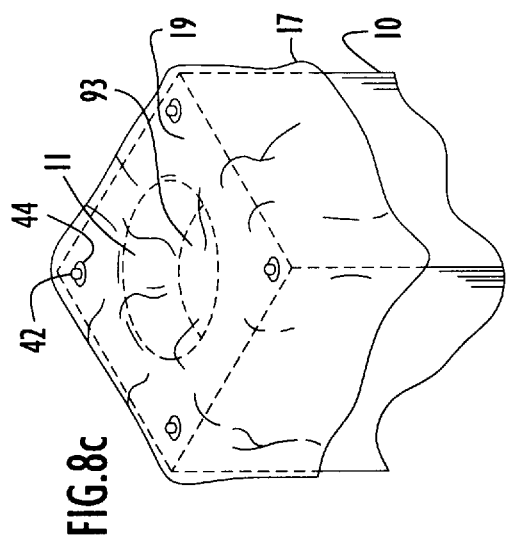
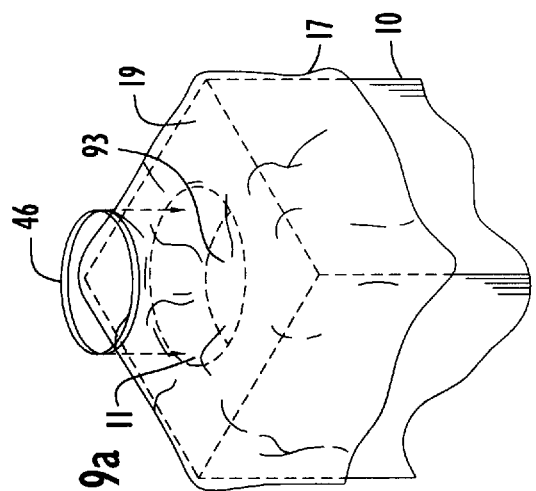
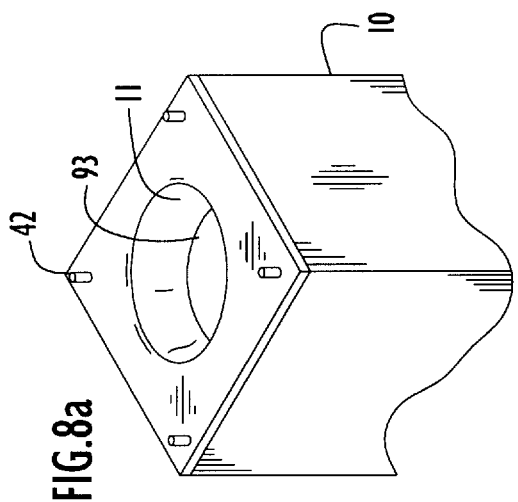
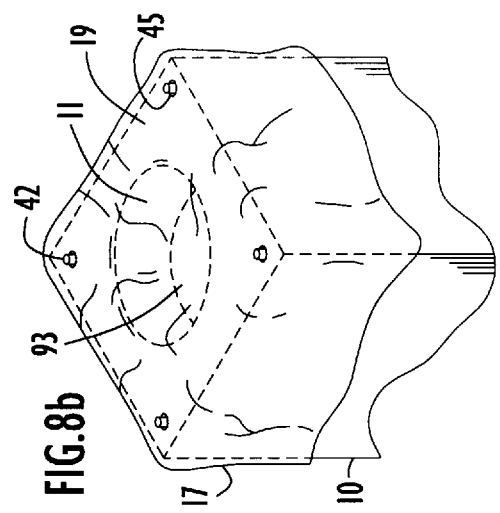

SURGICAL DRAPE FOR USE WITH SURGICAL SLUSH MACHINES HAVING AN AUTOMATIC DISLODGEMENT MECHANISM

BACKGROUND OF THE INVENTION

1. Technical Field

The present invention pertains to improvements in methods and apparatus for producing and collecting surgical sterile slush. In particular, the invention is an improvement of the methods and apparatus disclosed in U.S. Pat. Nos. 4,393,659 (Keyes et al), 4,934,152 (Templeton), 5,163,299 (Faries, Jr. et al), 5,331,820 (Faries, Jr. et al) and the patents cited therein. The disclosures in the aforementioned patents are expressly incorporated by reference herein in their entireties.

2. Discussion of the Prior Art

The above-referenced Keyes et al patent discloses a surgical slush producing system having a cabinet with a heat transfer basin at its top surface. A refrigeration mechanism in the cabinet takes the form of a closed refrigeration loop including an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use that space contains a thermal transfer liquid, such as alcohol or glycol, serving as a thermal transfer medium between the two basins. A sterile drape, impervious to the thermal transfer medium is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton patent, the Keyes et al system has a number of disadvantages. In particular, the separate product basin must be removed and resterilized after each use. Additionally, the glycol or other thermal transfer medium is highly flammable or toxic and, in any event, complicates the procedure. The Templeton patent discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al U.S. Pat. No. (5,163,299) notes that scraping congealed liquid from the drape is undesirable in view of the potential for damage to the drape, resulting in a compromise of sterile conditions. As a solution to the problem, the patent proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel.

The aforesaid Faries, Jr. et al U.S. Pat. No. (5,331,820) addresses the problem of removing the congealed liquid from the sides of the conformed drape receptacle in a surgical slush machine. Specifically, the drape is conformed to a cooled basin to establish a sterile field above the basin. The conformed drape receptacle collects a congealed sterile liquid (e.g., saline) in a sterile slush-like consistency. The congealed liquid tends to attach to sides of the drape receptacle in large clumps or pieces rather than automatically collecting within the drape receptacle interior. The Faries. Jr. et al U.S. Pat. No. (5,331,820) discloses a technique for automatically manipulating the drape relative to the basin wall to thereby cause the congealed liquid to detach from the drape receptacle sides and collect interiorly as desired slush. Briefly, the technique includes reciprocating the bottom of the conformed drape receptacle up and down to thereby loosen attached pieces of frozen saline from the sides of the drape receptacle.

The present invention is an improvement in the drape for use in conjunction with the aforementioned technique of reciprocating the bottom of the drape receptacle up and down to loosen pieces of frozen saline from the sides of the drape receptacle. It has been discovered that drapes having either a preformed container portion, made of other drape materials or formulations of the drape material currently being used (described below), or made of the conventional drape material and having a coefficient of friction less than approximately 0.4 when measured against steel (i.e., the basin) per ASTM 1983, are not effective for having the congealed liquid detached from the sides of the drape receptacle by reciprocating the bottom of the drape receptacle. Typically, the reciprocating motion is accomplished by a substantially circular plate or disc disposed at the bottom of the basin beneath the drape. The plate is reciprocally driven up and down to manipulate the drape receptacle relative to the basin to dislodge the congealed liquid from the sides of the drape receptacle. However, if the drape has a preformed container portion, the container portion becomes contoured to the basin and does not permit air to flow beneath the drape. The reciprocating motion of the plate creates a suction and draws the air between the drape and the plate, and the drape itself, beneath the plate. Similarly, if the drape is constructed of other drape materials or formulations of the conventional drape material, or the conventional drape material having a coefficient of friction less than approximately 0.4 as measured against steel per ASTM 1983, the resultant drape is slippery and becomes substantially contoured the basin to inhibit air from flowing beneath the drape. The suction created during the plate's reciprocating motion tends to draw the drape beneath the plate as described above. When the drape is positioned beneath the plate, the plate only manipulates that portion of the drape receptacle in contact with the plate, thereby leaving substantial parts of the drape receptacle unmanipulated with the congealed liquid attached.

OBJECTS AND SUMMARY OF THE INVENTION

Accordingly, it is an object of the present invention to secure a surgical drape to a surgical slush machine such that only a portion of the drape sufficient to form a drape receptacle is permitted to be disposed in the slush machine basin, thereby enabling a reciprocating plate to manipulate the drape receptacle and dislodge congealed liquid without having the drape slide beneath the plate.

It is another object of the present invention to secure a surgical drape to a surgical slush machine via stirrups of a precise length allowing only a portion of the drape sufficient to form a drape receptacle to be disposed in the slush machine basin, thereby enabling a reciprocating plate to manipulate the drape receptacle and dislodge congealed liquid without having the drape slide beneath the plate.

Yet another object of the present invention is to secure a surgical drape, having a skirt with locator bands, to a surgical slush machine including clamp-on bands for engaging the locator bands such that only a portion of the drape sufficient to form a drape receptacle is permitted to be disposed in the slush machine basin, thereby enabling a reciprocating plate to manipulate the drape receptacle to dislodge congealed liquid without having the drape slide beneath the plate.

Still another object of the present invention is to secure a surgical drape to a surgical slush machine via a formed band engaging the machine housing sides such that the formed band permits only a portion of the drape sufficient to form a drape receptacle to be disposed in the slush machine basin, thereby enabling a reciprocating plate to manipulate the drape receptacle and dislodge congealed liquid without having the drape slide beneath the plate.

A further object of the present invention is to secure a surgical drape, having a preformed container portion with ribs or ridges, to a surgical slush machine such that the preformed container portion is disposed in the surgical slush machine basin to permit air to flow beneath the drape and enable a reciprocating plate to manipulate the drape and dislodge congealed liquid without having the drape slide beneath the plate.

Yet another object of the present invention is to form a surgical drape for a surgical slush machine from either the conventional drape material described below having a coefficient of friction of approximately 0.4–1.0 as measured against steel per ASTM 1983, other drape materials or formulations of the conventional drape material having a securing mechanism to secure the drape to the machine, or a metalocine-based olefin film having a flexibility of approximately 10K–12K psi secant modulus measured by ASTM D882 while enabling a reciprocating plate to manipulate the drape and dislodge congealed liquid from the sides of the drape without having the drape slide beneath the plate.

Still another object of the present invention is to secure a surgical drape having a skirt of a precise length to a surgical slush machine such that the skirt permits only a portion of the drape sufficient to form a drape receptacle to be disposed in the slush machine basin, thereby enabling a reciprocating plate to manipulate the drape receptacle and dislodge congealed liquid without having the drape slide beneath the plate.

Yet another object of the present invention is to secure a surgical drape to a surgical slush machine having posts disposed on a top surface of the machine for receiving openings defined in the drape wherein post covers secure the drape to the posts such that only a portion of the drape sufficient to form a drape receptacle is permitted to be disposed in the slush machine basin, thereby enabling a reciprocating plate to manipulate the drape receptacle to dislodge congealed liquid without having the drape slide beneath the plate.

Still another object of the present invention is to secure a surgical drape to a surgical slush machine via a fixing ring disposed within a drape receptacle formed in the slush machine basin to maintain the drape position within the basin, thereby enabling a reciprocating plate to manipulate the drape receptacle to dislodge congealed liquid without having the drape slide beneath the plate.

A further object of the present invention is to secure a surgical drape to a surgical slush machine via an adhesive disposed on the drape and/or the top surface of the machine such that subsequent to disposing the drape in a slush machine basin to form a drape receptacle, the adhesive maintains the drape position within the basin, thereby enabling a reciprocating plate to manipulate the drape receptacle to dislodge congealed liquid without having the drape slide beneath the plate.

The aforesaid objects are achieved individually and in combination, and it is not intended that the present invention be construed as requiring two or more of the objects to be combined unless expressly required by the claims attached hereto.

According to the present invention, a surgical drape for use with a surgical slush machine having a reciprocating plate to manipulate the drape and dislodge congealed liquid is accomplished by a drape constructed of the conventional drape material described below and having a coefficient of friction in the range of approximately 0.4–1.0 as measured against steel (i.e. the basin) per ASTM 1983. Drapes having a coefficient of friction in that range typically generate frictional forces with the basin sufficient to prevent the drape from sliding beneath the reciprocating plate. Further, the drape may be constructed from a metalocine-based olefin film having a specific flexibility (i.e., approximately 10K–12K psi secant modulus measured by ASTM D882) to enable the drape to conform to the basin while being sufficiently rigid to permit air to flow between the plate and drape. The air flow prevents the drape from being drawn beneath the plate by a suction created by the motion of the reciprocating plate.

Alternatively, the drape may either be constructed of other drape materials or formulations of the conventional drape material, or the conventional drape material having a coefficient of friction below the range described above with various securing mechanisms to secure the drape to the machine cabinet. Further, the drape may include a preformed container portion having ribs or ridges to allow air to flow between the plate and the drape. The securing mechanisms and the preformed container portion with ribs or ridges prevent the drape from sliding beneath the reciprocating plate, thereby enabling substantial manipulation of the drape and dislodgement of the congealed liquid. Specifically, the drape having a securing mechanism includes a drape portion for covering a top surface and being pushed down into, and conforming to, a slush machine basin to form a drape receptacle. The drape portion hangs down over, and partially covers, the sides of the cabinet, with a skirt of precise length extending from the drape portion to cover the remaining uncovered surfaces of the sides of the cabinet. The skirt includes locator bands disposed at the ends of the skirt hanging down the sides of the cabinet adjacent the cabinet bottom to engage a respective lower corner of the cabinet. The locator bands engage respective lower cabinet corners to secure the drape to the machine such that the skirt permits only a part of the drape sufficient to form a drape receptacle to be disposed in the basin, thereby preventing the drape from sliding beneath the reciprocating plate.

Another embodiment of the drape having a securing mechanism includes a drape portion as described above and a shortened skirt extending from the drape portion having locator bands disposed at the ends of the skirt hanging down the sides of the cabinet. The locator bands engage respective clamp-on bands disposed on each side of the cabinet. The shortened skirt has a precise length to permit only a part of the drape sufficient to form a drape receptacle to be disposed in the basin, thereby preventing the drape from sliding beneath the reciprocating plate.

Yet another embodiment of the drape having a securing mechanism includes a drape portion as described above with stirrups attached to the drape portion to engage a respective lower corner of the cabinet and secure the drape to the machine. The stirrups have a precise length and permit only a part of the drape sufficient to form a drape receptacle to be disposed in the basin, thereby preventing the drape from sliding beneath the reciprocating plate.

Still another embodiment of the drape having a securing mechanism includes a drape portion as described above terminating in a formed band fitted to accommodate, and in frictional relation with, the cabinet sides. The band is slid over the machine and down the sides of the cabinet a precise distance to allow only a part of the drape sufficient to form a drape receptacle to be disposed in the basin, thereby preventing the drape from sliding beneath the reciprocating plate. Alternatively, the band may include stirrups to further secure the drape to the cabinet. The stirrups extend from the band down the sides of the cabinet to engage respective lower corners of the cabinet.

A further embodiment of the drape having a securing mechanism includes a drape portion as described above having openings defined therein for receiving posts disposed on a top surface of a surgical slush machine. The drape is fastened to the posts via post covers to secure the drape to the machine. The posts and corresponding drape openings are positioned such that only a portion of the drape sufficient to form a drape receptacle is permitted to be disposed in the basin, thereby preventing the drape from sliding beneath the reciprocating plate.

Yet another embodiment of the drape having a securing mechanism includes a drape portion as described above and a fixing ring for disposal in the basin. The fixing ring may be a separate unit, or disposed integral with the drape. A portion of the drape sufficient to form a drape receptacle is disposed in the basin with the fixing ring disposed within the basin about the perimeter of the drape receptacle. The ring secures portions of the drape coincident the ring tightly against the basin wall to maintain the drape position within the basin, thereby preventing the drape from sliding beneath the reciprocating plate.

Still another embodiment of the drape having a securing mechanism includes an adhesive disposed on either a top surface of the slush machine or the drape. A portion of the drape sufficient to form a drape receptacle is disposed in the basin with the adhesive securing the drape to the machine. The adhesive maintains the drape position within the basin, thereby preventing the drape from sliding beneath the reciprocating plate.

A further embodiment of the drape includes a drape portion terminating in a formed band as described above, and a preformed container portion fitted to match the contour of, and for being disposed within, the basin having ribs or ridges disposed in the walls of the container portion. The ribs or ridges provide a channel for air to flow along the basin beneath the drape to inhibit a suction created bib the motion of the reciprocating plate and thereby prevent the drape from being drawn beneath the plate. The band is fitted to accommodate, and in frictional relation with, the cabinet sides and is slid over the machine and down the sides of the cabinet to secure the drape to the cabinet.

The above and still further objects, features and advantages of the present invention will become apparent upon consideration of the following detailed description of a specific embodiment thereof, particularly when taken in conjunction with the accompanying drawings wherein the reference numerals in the various figures are utilized to designate like components.

BRIEF DESCRIPTION OF THE DRAWINGS

FIG. 7a is an exploded view of a surgical drape fitting over the surgical slush machine of FIG. 1 wherein the drape includes a drape portion and a formed band engaging the machine cabinet sides according to the present invention.

FIG. 7b is a view in perspective of the surgical drape and slush machine of FIG. 7a with the drape disposed on the machine according to the present invention.

FIG. 7c is a view in perspective of the surgical drape and slush machine of FIG. 7b wherein the drape includes stirrups attached to the formed band according to the present invention.

FIG. 8a is a view in perspective of the surgical slush machine of FIG. 1 having a plurality of posts disposed on the top surface of the machine according to the present invention.

FIG. 8b is a view in perspective of a surgical drape disposed on the slush machine of FIG. 8a such that posts of the slush machine are disposed through corresponding openings defined in the drape according to the present invention.

FIG. 8c is a view in perspective of the surgical drape and slush machine of FIG. 8b having post covers securing the drape to the machine according to the present invention.

FIG. 8d is a side view in elevation and partial section of an exemplary post cover according to the present invention.

FIG. 9a is an exploded view of a surgical drape disposed on the surgical slush machine of FIG. 1 with a fixing ring placed over, and for disposal within, the basin according to the present invention.

FIG. 9b is a view in perspective of the surgical drape and slush machine of FIG. 9a with the fixing ring disposed in the basin according to the present invention.

FIG. 11 is a view in perspective of a surgical drape having a drape portion, a preformed container portion including ribs or ridges, and a formed band for engaging the machine cabinet sides disposed on the surgical slush machine of FIG. 1 according to the present invention.

DETAILED DESCRIPTION OF THE PREFERRED EMBODIMENTS

Figure 1:
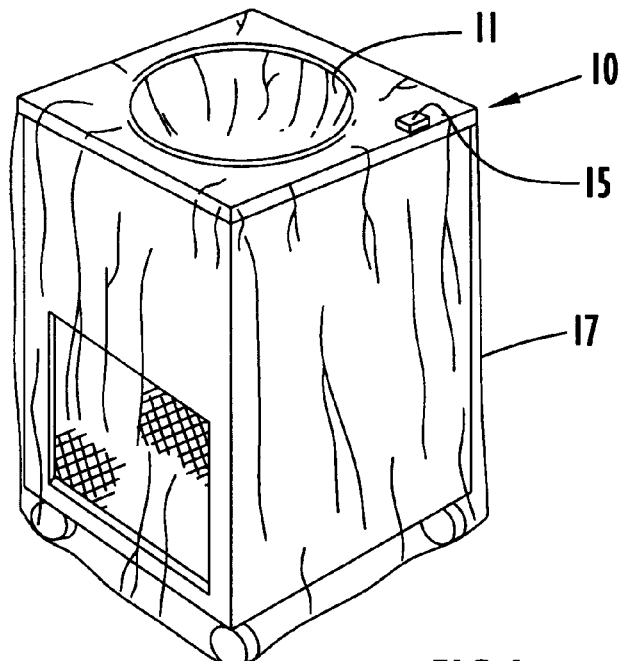
FIG. 1 is a view in perspective of a surgical slush machine of the type employed in the present invention.
Figure 2:
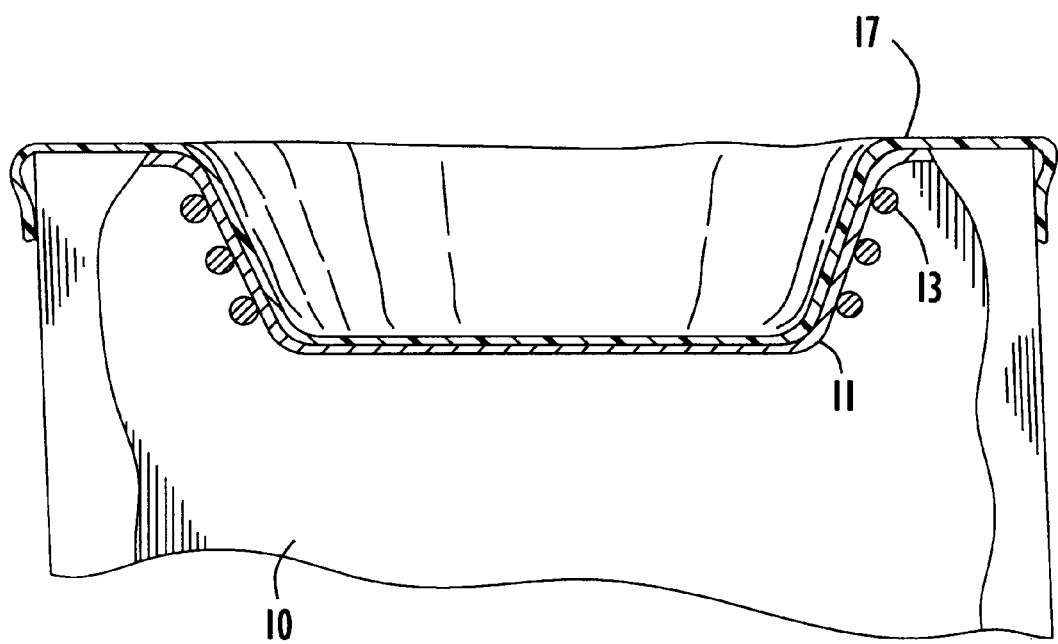
FIG. 2 is an elevational view in partial section of a surgical drape disposed in a basin of the surgical slush machine of FIG. 1 forming a drape receptacle.

Referring to FIGS. 1–2 of the accompanying drawings, a surgical slush generating system of the type described in the above-reference Templeton patent includes a cabinet or housing 10 with a top surface having a basin 11 mounted thereon in an appropriately sized recess. Basin 11 is made of thermally conductive material, typically stainless steel, and includes a generally flat bottom wall and frusto-conical side wall. The conventional refrigeration unit is disposed within cabinet 10 and typically includes a compressor, a condenser and an expansion control unit connected by appropriate fluid conduits in a closed refrigeration loop of evaporator 13. The evaporator is in the form of a coil wound about the exterior surface of basin 11 in thermal transfer relation therewith. The refrigeration unit is activated by means of appropriate controls 15, and evaporator 13 cools the side wall of basin 11 to a temperature substantially belong the freezing temperature of the liquid used in forming the sterile slush. This temperature is preferably in the order of –32° F. to 10° F. For further details of the structure and operation of the refrigeration unit, reference is made to the aforementioned Keyes et al and Templeton et al patents.

A sterile drape 17, preferably transparent, is disposed over the top and sides of cabinet 10 and made to conform to the side wall and bottom of basin 11. The portion of drape 17 disposed in the basin serves as a sterile receptacle for sterile liquid placed therein to be frozen into the desired sterile slush. Typical sterile liquid used for this purpose is a 0.80% to 0.95% sodium chloride solution (i.e., saline). Drape 17 is made from a material that is impervious to the sterile liquid and sufficiently soft and flexible to conform to the basin wall. The drape may also have a preformed container portion contoured to match the contour of the basin. The thickness of the drape is preferably minimized to render thermal transfer therethrough most efficient, yet the thickness is sufficient to resist tearing and puncturing during normal use. Typically, by way of example only, the drape may be made of materials commonly used in hospitals for surgical drapes and has a thickness in the range of 3.0 to 10.0 mils. Drape 17 may also be made of polyurethane film as disclosed for the drape in the aforementioned Templeton patent. The preformed container portion is typically thicker than the remaining portions of the drape described above in order to resist puncture and enable the container portion to maintain the shape of the basin. By way of example only, the container portion may be made of a heavy gauge polyethylene/ionomer resin blend having a thickness of approximately ten through sixteen mils. The percentage of ionomer resin in the blend is approximately in the range between forty and seventy percent. The drape is designed to be disposable after a single use and is provided presterilized and prepackaged in a manner to preserve its sterile state during storage.

Figure 3A:
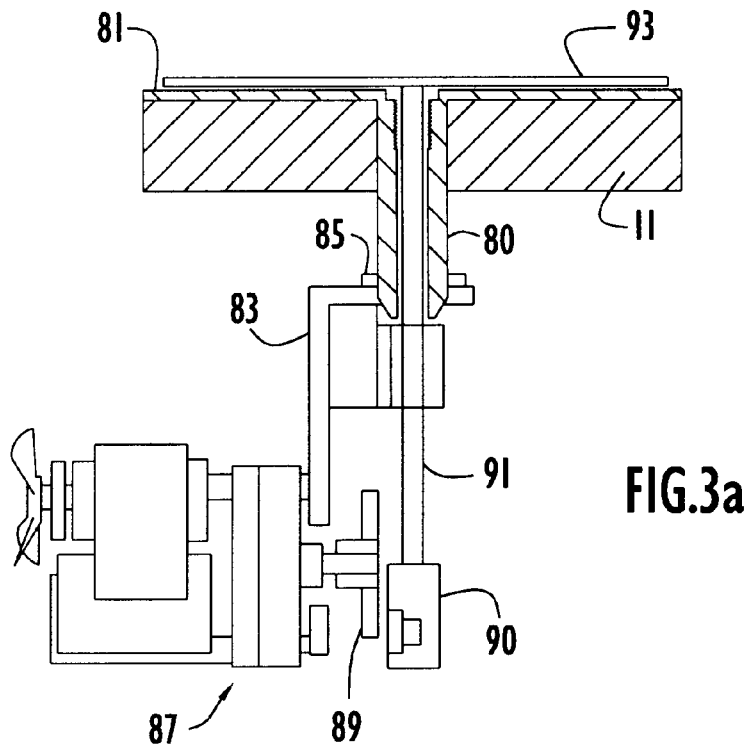
FIGS. 3a and 3b are diagrammatic illustrations in elevation and partial section of the reciprocating plate for manipulating a sterile drape in a surgical slush machine, the two figures showing the mechanism during different portions of its sequence of operation.
Figure 3B:
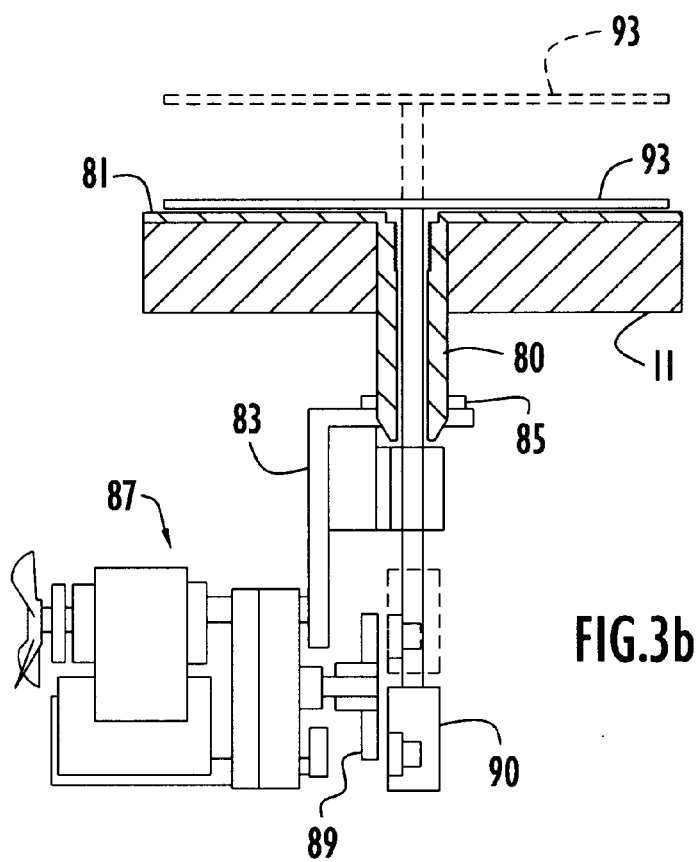

When the surgical slush machine is operating, the sterile liquid in the drape container freezes in pieces on the side walls of that container. In order to dislodge these frozen pieces so as to form sterile slush within the drape container, the surgical slush machine employs a reciprocating mechanism as shown in FIGS. 3a–3b. Specifically, substantially circular plate or disc 93 is disposed between the drape 17 (FIG. 2) and the bottom wall of basin 11. Disc 93 is horizontally oriented and substantially centered at the bottom of the basin, and the top surface of disc 93 is in contact with the underside of drape 17. The bottom of basin 11 is provided with a central hole through which an adapter tube 80 extends. Adapter tube 80 has an annular flange 81 extending radially outward from the upper end of the tube and positioned to rest on the bottom wall of the basin between the basin and the drape container (not shown). The bottom end of adapter tube 80 is externally threaded and is engaged by a support bracket 83 and lock washer 85 such that bracket 83 is suspended interiorly of the machine cabinet (not shown). A motor assembly, generally designated at 87, is supported by bracket 83 and includes a rotor 89 operatively engaged with a bearing track 90. A drive shaft 91 has its bottom end operatively engaged to bearing track 90 to cause the shaft to reciprocate longitudinally as rotor 89 rotates. Shaft 91 extends upwardly to adapter tube 80 and has its upper end secured to the center of the underside of plate 93 disposed between the adapter tube flange 81 and the bottom of the drape receptacle (not shown). Accordingly, as motor 87 reciprocates shaft 91 up and down, the shaft moves plate 93 up and down. The plate, in turn, moves the bottom of the drape container up and down to loosen attached pieces of frozen saline.

The above-mentioned reciprocating mechanism fully performs its intended function of dislodging congealed liquid when used with the drape (not including the preformed container portion) described above and having a coefficient of friction in the range of approximately 0.4–1.0 as measured against steel (i.e., the basin) per ASTM 1983. However, it the drape is adequately slippery (i.e., made of other drape materials or formulations of the conventional drape material. or made of the conventional drape material having a coefficient of friction less than the above-mentioned range), the reciprocating motion of the plate tends to draw parts of the drape beneath the plate, thereby inhibiting manipulation of the drape and dislodgement of the congealed liquid. This results from the fact that slippery drapes tend to be extremely flexible and substantially conform to the contour of the basin, thereby preventing air from residing and flowing between the plate and the drape. Further, drapes having a preformed container portion as described above similarly conform to the contour of the basin and prevent air from flowing between the plate and the drape. The motion of the reciprocating plate creates a suction by drawing the air in the space between the plate and the drape beneath the plate, thereby causing the drape to follow. When the drape is drawn beneath the plate, the plate merely manipulates parts of the drape in contact with the plate at the approximate center of the basin and does not dislodge congealed liquid on the side walls of the drape container. Sticky drapes (i.e., drapes having a coefficient of friction greater than the above mentioned range), on the other hand, are less flexible and form folds when disposed in the basin. The folds form channels to permit air to flow beneath the drape and inhibit the formation of the suction. Sticky drapes function well with the reciprocating mechanism to dislodge congealed liquid, but are extremely difficult to unfold and do not fully conform to the basin shape.

A suitable material for forming and enabling the drape to function with the reciprocating mechanism is, for example, a metalocine-based olefin film. This film has a specific flexibility in the approximate range between 10k and 12k psi secant modulus measured by ASTM D882. The flexibility value indicates that a drape formed from this film is rigid enough to form folds in the basin and allows air to flow beneath the drape (to prevent formation of the suctioii described above), yet flexible enough to substantially conform to the basin. In other words, the resulting drape has the favorable properties of both the above mentioned sticky and slippery drapes, and therefore, functions with the reciprocating plate to dislodge congealed liquid.

Figure 4A:
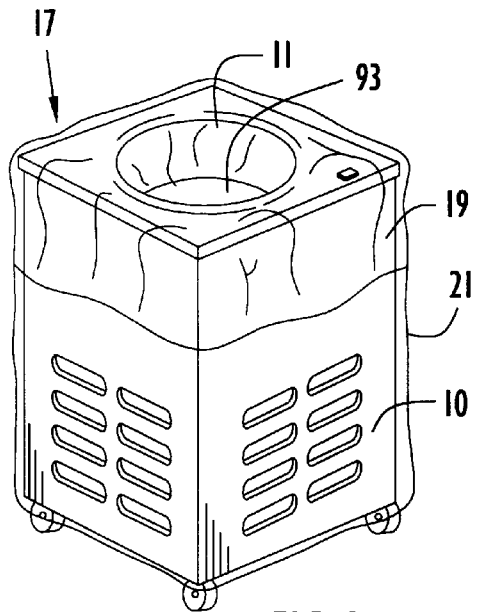
FIG. 4a is a view in perspective of a surgical drape disposed on the surgical slush machine of FIG. 1 having a drape portion and a skirt of precise length according to the present invention.
Figure 4B:
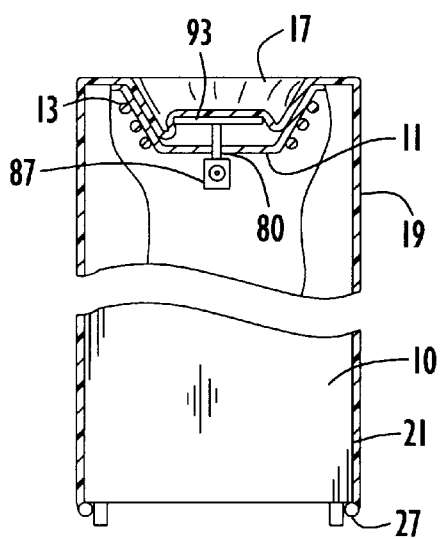
FIG. 4b is a view in elevation and partial section of the surgical drape and slush machine of FIG. 4a wherein locator bands disposed at the ends of the skirt proximate lower corners of the machine cabinet secure the drape to the slush machine according to the present invention.

The slippery drapes described above are typically preferable due to their lower costs and substantial conformance to the contour of the basin. In order to maintain such drapes above the reciprocating plate, the present invention utilizes several securing mechanisms to secure the drape to the machine housing and allow only parts of the drape sufficient to conform to the basin and form a drape receptacle to be disposed within the basin. The basin therefore contains only the amount of the drape necessary to form the receptacle, thereby leaving no margin for any excess portions of the drape to be drawn beneath the reciprocating plate. FIGS. 4a–4b illustrate such a drape having a precise length to allow only parts of the drape sufficient to form the drape receptacle to be disposed in the basin without leaving any margin for excess portions of the drape to be drawn beneath the plate. Specifically, drape 17 includes a drape portion 19 and skirt 21 with locator bands 27 disposed on skirt 21 to engage respective bottom corners of cabinet 10. The surgical slush machine is substantially similar to the machine of FIG. 1 having the reciprocating plate mechanism of FIGS. 3a–3b to dislodge congealed liquid as described above. The height of cabinet 10 relative to the floor is approximately thirty-two inches with a substantially square top surface having a width and length of approximately eighteen inches. Other cabinets having various top surface dimensions may be used with an adapter to yield a top surface dimension substantially similar to that of the machine described above. Drape portion 19 may be made of any liquid impervious materials, or formulations of the materials described above, while skirt 21 may be made of cloth or other suitable material to secure the drape to the machine. Drape portion 19 covers the top surface of cabinet 10 and is pushed down into, and conforms to, basin 11 to form a drape receptacle. Drape portion 19 partially hangs down from the top surface and along the sides of cabinet 10 for approximately one-quarter the height of the cabinet where skirt 21 is attached to the drape portion. Skirt 21 may be attached to drape portion 19 by any conventional attachment process, and extends from the drape portion to the bottom of cabinet 10 while covering the remaining surfaces of the cabinet sides. A plurality of locator bands 27 are disposed on the edges of skirt 21 adjacent the bottom of cabinet 10 with each band corresponding to a respective bottom corner of the cabinet. Locator bands 27 are typically a disposable part of drape 17, but may be reusable and separate units apart from drape 17 wherein the bands are removably attached to the drape by a conventional fastening mechanism. Locator bands 27 may be semi-elastic and substantially looped members in order to engage the bottom corners of cabinet 10 and secure drape 17 to the machine. Any number of locator bands 27 may be disposed on skirt 21, but four is preferable to tightly secure the drape to the machine. Skirt 21 is constructed to a precise length such that when drape 17 is disposed on, and secured to, cabinet 10 via locator bands 27, there is only a sufficient amount of drape portion 19 disposed in basin 11 to form and maintain the drape receptacle without leaving any margin for excess portions of the drape to be drawn beneath reciprocating plate 93 (i.e., the drape is secured to the machine to prevent it from sliding beneath the plate). This enables plate 93 to manipulate the sides of the drape receptacle and dislodge the congealed liquid.

Figure 5:
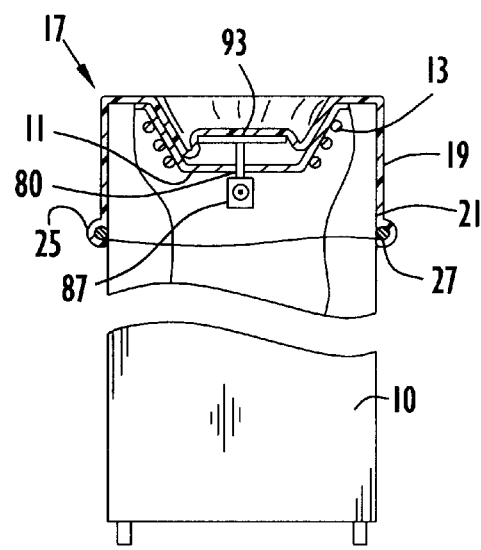
FIG. 5 is a view in elevation and partial section of a surgical drape including a drape portion and a shortened skirt of precise length with locator bands disposed on a surgical slush machine having clamp-on bands disposed on machine cabinet sides to engage the locator bands according to the present invention.

Alternatively, drape 17 may be utilized with a shortened skirt as illustrated in FIG. 5. The surgical slush machine and drape are substantially similar to the surgical slush machine and drape described above except that the drape includes a shortened skirt, and the machine includes clamp-on bands disposed on the cabinet sides. Drape 17 includes a drape portion 19 and shortened skirt 21 having a plurality of locator bands 27 disposed on the shortened skirt. Locator bands 27 are typically a disposable part of drape 17 and may be semi-elastic looped members for engaging and securing the drape to cabinet 10 as described below. Alternatively, locator bands 27 may be reusable and separate units apart from drape 17 wherein the bands are removably attached to the drape by a conventional fastening mechanism. Cabinet 10 includes clamp-on bands 25 disposed on each of the four sides of the cabinet at the approximate widthwise center of the respective side, and at a height of approximately three-quarters the height of the cabinet. Any number of clamp-on bands 25 and corresponding locator bands 27 may be respectively disposed on cabinet 10 and shortened skirt 21, but four is preferable to secure the drape tightly to the cabinet. Clamp-on bands 25 are typically reusable and remain disposed on the sides of cabinet 10, and include a conventional hook or a clasping mechanism to engage a corresponding one of the locator bands 27. Drape portion 19 covers the top surface of cabinet 10, and is pushed down into, and conforms to, basin 11 to form a drape receptacle as described above. Drape portion 19 hangs down from the top surface and along the sides of cabinet 10 for approximately one-eighth of the height of the cabinet where shortened skirt 21 is attached to the drape portion. Shortened skirt 21 may be attached to drape portion 19 by any conventional attachment process, and is substantially similar to the skirt described above. Shortened skirt 21 extends from drape portion 19 for approximately one-eighth the height of cabinet 10 to the point where clamp-on bands 25 are disposed on the cabinet sides. Locator bands 27 are disposed on the shortened skirt such that each locator band is positioned adjacent, and corresponds to, a respective clamp-on band 25. Each of the locator bands 27 engage a corresponding clamp-on band 25 to secure the drape to cabinet 10. Shorted skirt 21 is constructed to a precise length such that when locator bands 27 secure drape 17 to cabinet 10, there is only a sufficient amount of drape portion 19 disposed in basin 11 to form and maintain the drape receptacle without leaving any margin for excess portions of the drape to be drawn beneath reciprocating plate 93 (i.e. the drape is secured to the machine to prevent it from sliding beneath the plate) as described above. Further, locator bands 27 may secure the drape to cabinet 10 by engaging the cabinet itself without the need for clamp-on bands 25.

Figure 6:
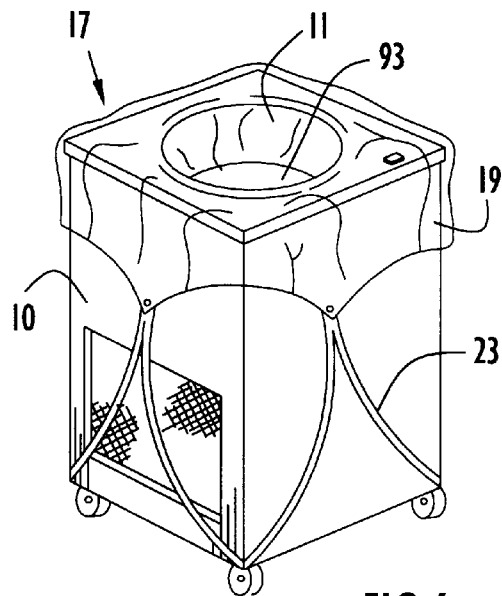
FIG. 6 is a view in perspective of a surgical drape having a drape portion and stirrups of precise length disposed on the surgical slush machine of FIG. 1 according to the present invention.

Another embodiment of the drape utilizing stirrups to secure the drape to the machine and prevent the drape from being drawn beneath the reciprocating plate is illustrated in FIG. 6. The surgical slush machine and drape are substantially similar to the surgical slush machine and drape having a full length skirt described above except that instead of using a skirt, the drape utilizes stirrups to secure the drape to the cabinet. Specifically, drape 17 includes drape portion 19 covering the top surface of cabinet 10 and being pushed down into, and conforming to, basin 11 to form a drape receptacle as described above. Drape portion 19 hangs down from the top surface and along the sides of cabinet 10 for approximately one-quarter the height of the cabinet. The edges of drape portion 19 hanging down the sides of cabinet 10 are shaped to form peaks on each side of, and pointing toward the bottom of, the cabinet at the approximate widthwise center of the respective side. A plurality of stirrups 23 are attached to drape portion 19 with each stirrup corresponding to a respective bottom corner of cabinet 10. Each of the plurality of stirrups 23 is typically a semi-elastic cord or band disposed on the drape to form a substantially looped member for engaging the corresponding bottom corners of cabinet 10. The drape may include any number of stirrups, but four is preferable to secure the drape at each corner of the cabinet. Stirrups 23 are disposed on the drape such that one end of a cord is attached to an apex of a peak while the other end of the cord is attached to an apex of an adjacent peak. The cords may be attached to drape portion 19 in any conventional manner including, but not limited to: fastening mechanisms, or tying the cords to the peaks via small openings defined in the peaks. The secured ends of the cord form a substantially looped member along the intermediate portion of the cord which engages a respective corner of cabinet 10. Each of the stirrups 23 is formed in this fashion such that each peak includes a cord end from two different stirrups. The different stirrups engage separate corners of cabinet 10 between which the peak is disposed. Stirrups 23 are constructed of a precise length to allow only a sufficient amount of drape portion 19 to be disposed in basin 11 to form and maintain the drape receptacle without leaving any margin for excess portions of drape 17 to be drawn beneath reciprocating plate 93 (i.e., the drape is secured to the machine to prevent it from sliding beneath the plate). Further, stirrups 23 may be reusable and separate units apart from drape 17 wherein the stirrups are removably attached to the drape by a conventional fastening mechanism. Moreover, stirrups 23 may have adjustable lengths to accommodate various sized slush machines by varying the length of the stirrups to control the amount of drape portion 19 permitted to be disposed in basin 11 to form the drape receptacle. The lengths of the stirrups are adjusted such that only parts of drape portion 19 sufficient to form and maintain the drape receptacle are disposed in basin 11 without leaving any margin for excess portions of the drape to be drawn beneath reciprocating plate 93 as described above.

Yet another embodiment of the drape having a formed band to secure the drape to the cabinet and prevent the drape from being drawn beneath the reciprocating plate is illustrated in FIGS. 7a–7c. The drape and surgical slush machine are substantially similar to the drape and surgical machine for the drape having a full length skirt described above except that the drape includes a formed band instead of a skirt for securing the drape to the cabinet. Specifically, drape 17 includes drape portion 19 covering the top surface of cabinet 10 and being pushed down into, and conforming to, basin 11 to form a drape receptacle as described above. Drape portion 19 partially hangs down the sides of cabinet 10 for approximately one-eighth the height of the cabinet. Formed band 29 is attached to drape portion 19 hanging down along the sides of cabinet 10 and typically extends from the drape portion down along the cabinet sides for approximately one-eighth the height of the cabinet. Formed band 29 typically matches the transverse cross-sectional shape of the cabinet (i.e., the shape of the top surface) and has slightly smaller dimensions than the cabinet perimeter such that the band tightly engages the cabinet sides to secure the drape to the cabinet. Formed band 29 is substantially semi-elastic and typically made of the same material as drape portion 19 which is tack welded to form the band. Drape 17 is disposed on cabinet 10 with formed band 29 slid down from the top surface of the cabinet in frictional relation with the cabinet sides. Drape portion 19 is pushed down into the basin to form the drape receptacle while formed band 29 tightly engages the sides of cabinet 10 such that the frictional forces between the cabinet sides and formed band 29 prevent the formed band and drape from sliding. Formed band 29 is positioned along the sides of cabinet 10 such that there is a sufficient amount of drape portion 19 disposed in basin 11 to form and maintain a drape receptacle without leaving any margin for excess portions of the drape to be drawn beneath reciprocating plate 93 (i.e., the drape is secured to the machine to prevent it from sliding beneath the plate).

Alternatively, formed band 29 may include a plurality of stirrups 23 (FIG. 7c), substantially similar to the stirrups described above, for securing drape 17 to cabinet 10. Each of the stirrups 23 disposed on the drape include a semi-elastic cord or band to form a substantially looped member along an intermediate portion of the cord for engaging a corresponding lower corner of cabinet 10. Formed band 29 may include any number of stirrups, but four is preferable to secure the drape at each corner of cabinet 10. Each of the cords forming stirrups 23 extend from formed band 29 to the bottom of cabinet 10 with one end of the cord attached to formed band 29 on a first side of the cabinet, an intermediate portion of the cord engaging a corresponding bottom corner of the cabinet and the other end of the cord attached to the formed band on an adjacent side of the cabinet which intersects the first side to form the corresponding, bottom corner. Formed band 29 therefore includes cord ends of two different stirrups on each respective side of cabinet 10 with the cord ends of the different stirrups attached to the formed band toward their respective engaged corners between which the respective side is disposed. Each of the stirrups 23 is disposed in this fashion to secure the drape to cabinet 10 such that there is a sufficient amount of drape portion 19 disposed in basin 11 to form and maintain the drape receptacle without leaving any margin for excess portions of drape 17 to be drawn beneath reciprocating plate 93 (i.e., the drape is secured to the machine to prevent it from sliding beneath the plate) as described above. Further, stirrups 23 may have adjustable lengths to accommodate various sized machines in substantially the same manner described above.

Still another embodiment of the drape utilizing posts and post covers for securing the drape to the surgical slush machine is illustrated in FIGS. 8a–8d. The surgical slush machine is substantially similar to the machine described above for FIG. 1 having the dislodgement mechanism of FIGS. 3a–3b except that the top surface of cabinet 10 includes a plurality of securing posts 42. Specifically, drape 17 is substantially similar to the drapes described above except that the drape only includes a drape portion 19 for covering the top surface and hanging down the sides of cabinet 10 for approximately one-quarter the height of the cabinet. A plurality of securing posts 42 are disposed on, and extend vertically from (i.e., in an upward direction), the top surface of cabinet 10. By way of example only, four securing posts 42 are disposed on the top surface of cabinet 10 such that the posts surround basin 11 with each post proximate a respective corner of the top surface. However, there may be any number of posts arranged in any fashion capable of maintaining drape 17 within basin 11 as described below.

Posts 42 are typically short substantially cylindrical stubs, and extend vertically (i.e., upwardly) from the top surface of cabinet 10 for a length sufficient to traverse the thickness of the drape and receive post covers 44 to secure the drape to the cabinet. Posts 42 may be of any cross-sectional shape (e.g., circular, polygonal, elliptical), and may be constructed of metal, plastic, rubber or other sturdy material. Further, posts 42 may include threading (not shown) to securely receive cover 44 and positively attach the drape to the machine as described below.

In order to utilize posts 42, drape 17 further includes a plurality of openings 45 defined in the drape such that each of the openings correspond to one of the posts 42. Openings 45 may be of any shape enabling posts 42 to traverse the respective opening, and are defined at locations on the drape corresponding to the positions of posts 42 on the top surface of cabinet 10. Openings 45 are located on, and define the boundaries of, the portion of drape 17 which is to be disposed in the basin to form the drape receptacle. Drape 17 is typically disposed over the top surface of cabinet 10 such that posts 42 traverse corresponding openings 45 with the portion of the drape surrounded by the openings being disposed in the basin to form a drape receptacle. Posts 42 and openings 45 are positioned on the top surface of cabinet 10 and the drape, respectively, such that only a portion of the drape sufficient to form a drape receptacle is permitted to be disposed in the basin without leaving any margin for excess portions of the drape to be drawn beneath reciprocating plate 93.

Once drape 17 is disposed on the machine, sterile covers 44 are disposed on corresponding posts 42 to secure the drape to the machine and maintain the sterile field and drape position about the basin. Covers 44, by way of example only, include a short substantially hollow cylindrical portion 52 having a rounded proximal end and a brim 50 disposed about the perimeter of its open distal end (i.e., the cylindrical portion includes an opening at its distal end for reception of the post). Brim 50 typically lies flush against drape 17 when cover 44 is disposed on post 42 to maintain the drape against the top surface of cabinet 10. Cylindrical portion 52 receives the distal portion of a corresponding ,post 42 when the cover is placed on the post to secure the drape to the machine. Cylindrical portion 52 may have a cross-sectional diameter slightly less than the cross-sectional dimensions of a corresponding post 42 such that cover 44 is securely fastened to the post. In this instance, cover 44 is typically made of plastic, rubber, or other suitably flexible material in order to accommodate the dimensions of, and cover, the post. Alternatively, the cross-sectional diameter of cylindrical portion 52 may be greater than the cross-sectional dimension of corresponding post 42 and may loosely cover the post. In this case, cover 44 has increased weight in order to securely fasten the drape against the top surface of cabinet 10 as described above.

It is to be understood that covers 44 are not limited to the embodiments described above but may be of any shape, dimension, or material capable of fitting over or around posts 42 to secure drape 17 to the machine. Further, any number of posts, covers, and corresponding openings may be used and arranged in any fashion capable of securing the drape to the machine. Moreover, the covers 43 described above may be utilized on either threaded or unthreaded posts 42. However, in order to achieve an improved fit when a post 42 is threaded, the interior surfaces of cylindrical portion 52 may also be threaded (not shown) to interleave with threads on the post. In this instance, cover 44 is aligned with post 42 such that the threads of cover 44 are interleaved with the threads of the post wherein the cover is subsequently rotated to be securely fastened to the post. Posts 42 and covers 44 secure the drape to the machine such that only a portion of the drape sufficient to form and maintain a drape receptacle is disposed in the basin without leaving any margin for excess portions of the drape to be drawn beneath reciprocating plate 93 (i.e., the drape is secured to the machine to prevent it from sliding beneath the plate), thereby enabling reciprocating plate 93 to manipulate the sides of the drape receptacle and dislodge congealed liquid.

A further embodiment of the drape utilizing a fixing ring or hoop to secure the drape to the machine is illustrated in FIGS. 9a–9b. The slush machine is substantially similar to the slush machine described above for FIG. 1 having the dislodgement mechanism of FIGS. 3a–3b. The drape is substantially similar to, and includes a drape portion 19 as described above for, the post embodiment drape, except that there are no openings defined in the drape. Specifically, a sterile fixing ring or hoop 46 is utilized to secure the drape to the machine and maintain the sterile field and drape position about the basin. Ring 46 may be either a separate unit, or disposed integral with the drape, and may be constructed by a rod or bar of any cross-sectional shape (e.g. circular, polygonal, elliptical) made of plastic, rubber, or other suitably rigid material formed into the shape of a particular basin in which the ring is to be disposed. The shape of ring 46 is typically substantially circular with dimensions slightly less than the cross-sectional dimensions of the basin, but may be of any shape to match the cross-sectional dimension of a particular basin. Drape 17 is typically disposed on a top surface of cabinet 10 such that drape portion 19 covers the top surface and hangs down the sides of the cabinet for approximately one-quarter the height of the cabinet. A portion of drape 17, sufficient to form a drape receptacle, is disposed in basin 11 without leaving any margin for excess portions of the drape to be drawn beneath reciprocating plate 93. Ring 46 is disposed in the basin such that the perimetric surfaces of the ring (i.e., the exterior surface of the ring along the perimeter) traverse the basin walls until the ring diameter exceeds the diameter of a section of frusto-conical basin 11. At this juncture, ring 46 presses portions of the drape receptacle coincident the ring firmly against the basin walls to secure the drape within the basin. Ring 46 maintains the drape receptacle position in the basin and prevents excess portions of the drape from sliding beneath reciprocating plate 93 during operation, thereby enabling reciprocating plate 93 to manipulate the drape receptacle and dislodge congealed liquid.

Alternatively, ring may be disposed integral with the drape such that the ring, encompasses the portion of the drape to be disposed in the basin, thereby a drape container similar to the preformed container portion described above. Specifically, ring 46 is disposed on the drape for insertion into a basin as described above. Ring 46 is situated such that the container portion includes only a portion of the drape sufficient to form a drape receptacle without leaving any margin for excess portions of the drape to be drawn beneath reciprocating plate 93. The drape is disposed on the machine with the container portion disposed in the basin. The perimetric surfaces of ring 46 traverse the basin walls until the ring diameter exceeds the diameter of a section of frusto-conical basin 11 as described above, wherein the ring firmly presses portions of the drape container against the basin walls. Ring 46 maintains the drape receptacle position in the basin (i.e., prevents the drape from sliding) in substantially the same manner described above to prevent excess portions of the drape from being drawn beneath reciprocating plate 93, thereby enabling the reciprocating plate to manipulate the drape container and dislodge congealed liquid.

Figure 10A:
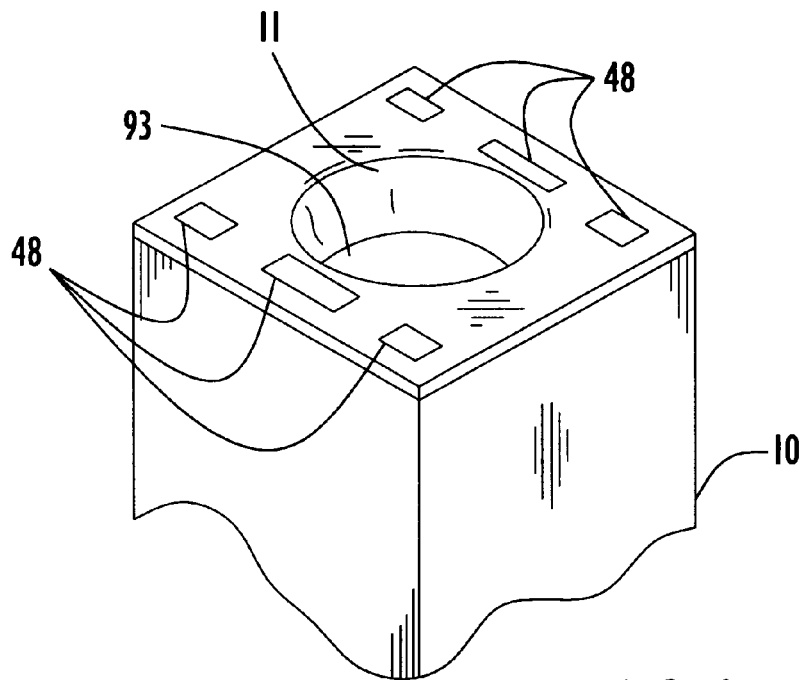
FIG. 10a is a view in perspective of the surgical slush machine of FIG. 1 having double-sided adhesive tape disposed on a top surface of the machine according to the present invention.
Figure 10B:
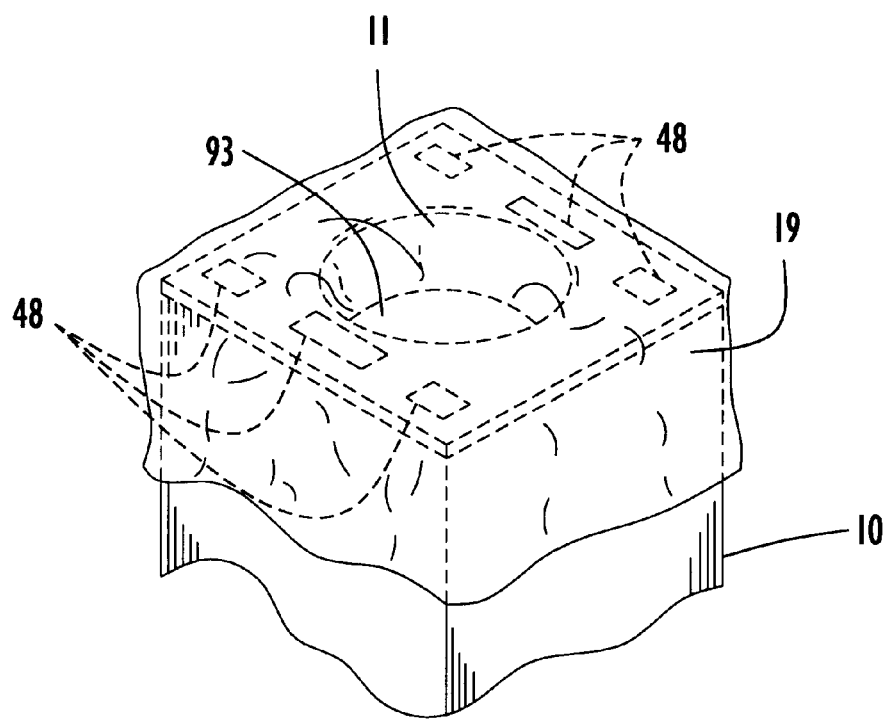
FIG. 10b is a view in perspective of a surgical drape disposed on the slush machine of FIG. 10a according to the present invention.

Yet another embodiment of the drape utilizing adhesives to secure the drape to the slush machine is illustrated in FIGS. 10a–10b. The slush machine is substantially similar to the slush machine described above for FIG. 1 having the dislodgement mechanism of FIGS. 3a–3b, except that the slush machine includes a plurality of adhesives disposed on the top surface of the machine. The drape is substantially similar to the drapes described above having only a drape portion 19. Specifically, cabinet 10 includes a plurality of adhesives disposed on its top surface. By way of example, the adhesives are segments 48 of double-sided adhesive tape, but any other adhesives may be used to removably attach the drape to the cabinet. Tape segments 48 are disposed on the top surface of cabinet 10 such that the tape surrounds basin 11. In this exemplary embodiment, six segments of tape are utilized, however, any number of segments of tape, or amounts of other adhesives capable of securing the drape to the machine may he used. Drape 17 is disposed on the machine such that drape portion 19 covers the top surface of the cabinet 10 and hangs down the sides of the cabinet for approximately one-quarter the height of the cabinet. A portion of drape 17 sufficient to form a drape receptacle is disposed in the basin without leaving any margin for excess portions of the drape to be drawn beneath reciprocating plate 93. After the drape is disposed in the basin, portions of the drape coincident tape segments 48 are firmly pressed against the tape segments to enable the tape segments to adhere to, and secure, the drape to the machine. Tape segments 48 maintain the drape position (i.e., prevents the drape from sliding) within the basin such that excess portions of the drape are not drawn beneath reciprocating plate 93 during operation, thereby enabling the reciprocating plate to manipulate the drape and dislodge congealed liquid. Further, tape segments 48 may be replaced with new segments or other adhesives when the tape segments' adhesive characteristics begin to dissipate.

Alternatively, tape segments 48 or other adhesives may be attached to the drape to prevent the drape from sliding beneath reciprocating plate 93 in substantially the same manner described above. Specifically, tape segments 48 are disposed on drape 17 such that the tape segments define the boundaries of, and encompass, a portion of the drape sufficient to form a drape receptacle within the basin without leaving any margin for excess portions of the drape to slide beneath reciprocating plate 93. The drape is disposed on the machine as described above such that the portion of the drape encompassed by the tape segments is disposed in the basin with tape segments 48 coincident the top surface of cabinet 10. Tape segments 48 are subsequently firmly pressed against the top surface such that tape segments 48 adhere to the top surface to secure the drape to the machine and maintain the drape position within the basin (i.e., prevent sliding). Tape segments 48 prevent excess portions of the drape from being drawn beneath reciprocating plate 93, thereby enabling the reciprocating plate to manipulate the drape and dislodge congealed sterile liquid.

When drapes having preformed container portions are utilized with the reciprocating plate mechanism described above, the container portions are disposed in the basin and effectively form a seal to prevent air from infiltrating the area between the container portion and reciprocating plate. The motion of the reciprocating plate draws the air in the space between the container portion and the drape beneath the plate and creates a suction which causes the container portion to be pulled beneath the plate as described above. A drape having a container portion with ribs or ridges to allow air to flow between the container portion and reciprocating plate to inhibit the formation of the suction and prevent the container portion from being drawn beneath the reciprocating plate is illustrated in FIG. 11. The surgical slush machine is substantially similar to the surgical slush machine described above for FIG. 1 having the dislodgement mechanism of FIGS. 3c–3b. Specifically, drape 17 is substantially similar to the drape having a preformed container portion described above, and includes drape portion 19 covering the top surface of cabinet 10 and partially hanging down along the sides of the cabinet for approximately one-eighth the height of the machine, and a preformed container portion 31, fitted to match the contour of, and for being disposed within, basin 11. A formed band 29 is attached to the ends of drape portion 19 hanging down along the sides of cabinet 10 and is substantially similar in dimension and function, and is attached to drape portion 19 in substantially the same manner as, the formed band described above.

Container portion 31 includes ribs or ridges 33 disposed in the walls of the container portion substantially evenly spaced about its perimeter. Ribs 33 are typically formed by inward pinches in the drape (i.e., pinching from the interior of the container portion) causing concave inward, convex outward displacements similar to the displacements in the interior of a bundt cake pan. Ribs 33 extend from the basin floor to the top of the basin, and maintain parts of container portion 31 coincident ribs 33 away from the basin walls. Ribs 33 essentially form channels between the basin wall and container portion 31 to permit air to flow between the container portion and reciprocating plate 93. The air inhibits the formation of a suction by the motion of reciprocating plate 93, thereby preventing the container portion from being drawn beneath the plate and enabling the plate to manipulate the container portion and dislodge congealed liquid. Drape 17 is disposed on cabinet 10 with formed band 29 slid down, and in frictional relation with, the sides of the cabinet as described above. Formed band 29 secures the drape to the machine and is positioned on cabinet 10 such that container portion 31 is disposed in basin 11. Since ribs 33 allow air to flow between container portion 31 and reciprocating plate 93 to prevent formation of the suction, the reciprocating plate manipulates container portion 31 to dislodge congealed liquid as described above.

It will be appreciated that the embodiments described above and illustrated in the drawings represent only a few of the many ways of implementing a surgical drape for use with surgical slush machines having automatic dislodgement of congealed liquid.

The drapes may be made of the conventional drape material having the preferable coefficient of friction of approximately 0.4–1.0 as measured against steel per ASTM 1983, a metalocine-based olefin film having a flexibility in the approximate range of 10K–12K psi secant modulus measured by ASTM D882, or other suitable liquid impervious materials having a securing mechanism to prevent the drape from sliding beneath the plate. The securing mechanism may include any devices capable of securing the drape to the machine. The skirt and drape portion of drapes having a securing mechanism may cover the cabinet in any desired proportions as long as the specified length of the drape is maintained. The formed bands may be made of material used to make the drape or other material capable of securing the drape to the cabinet without slipping. The stirrups and or locator bands may be any semi-elastic or elastic material having a looped or other member for engaging the cabinet, and may be disposed anywhere on the drapes capable of securing the drape to the machine. Further, the locator bands or stirrups may be separate from the drape and reusable. Moreover, the stirrups may be adjustable to accommodate various sized cabinets. The clamp-on bands may be reusable and be any device disposed anywhere on the cabinet capable of engaging the locator bands to secure the drape to the cabinet. The container portion may include ribs, ridges, or any other objects formed in the drape to maintain space between the basin and the drape to allow air to flow between the drape and the plate to prevent the drape from being drawn beneath the plate. The ribs disposed in the container portion may be spaced in any fashion and thermo-formed, pinched or created by any other process forming the drape.

The posts may be implemented by any members extending from the top or other surfaces of the cabinet in any direction capable of securing the drape. Further, the covers may be of any shape and dimension capable of covering the post to secure the drape to the machine. Moreover, the posts may be utilized without covers (e.g., include hooking or other clasping mechanisms) to secure the drape to the machine. The drape openings for receiving the posts may be of any size or shape capable of receiving the posts. The posts, openings, and covers may be of any number and may be disposed in any arrangement or configuration capable of securing the drape to the machines. The posts and covers may be unthreaded, threaded or use any other arrangement to secure the covers to the posts. The fixing ring may be of any shape or dimension capable of securing the drape within the basin. In addition, the ring may be formed by any elongated member of any cross-sectional shape manipulated into any shape capable of securing the drape in the basin. The ring may be a separate unit or disposed integral with the drape and may be disposed in the basin at any orientation capable of securing the drape. Any type and amount of adhesive capable of removably attaching the drape to the machine, and being removably attached to the machine, may be used to secure the drape to the machine. The adhesive may be disposed on a top surface of the machine, or on the drape in any manner capable of securing the drape.

The present invention may be implemented by any process or drape wherein the drape is secured to any surgical slush machine cabinet such that excess portions of the drape are removed from the machine basin to prevent the drape from being drawn beneath a reciprocating plate (i.e. the drape is secured to the machine to prevent it from sliding beneath the dislodgement mechanism) or any other dislodgement mechanism disposed at the bottom of the basin for manipulating the drape. Further, the present invention may be implemented by any drapes allowing air to flow beneath the drape in a slush machine basin to prevent the formation of a suction drawing the drape beneath the reciprocating plate or other dislodgment mechanism disposed at the bottom of the basin.

From the foregoing description it will be appreciated that the invention makes available a novel surgical drape for use in a surgical slush machine having an automatic dislodgement mechanism wherein the surgical drape has either a certain coefficient of friction or flexibility, a securing mechanism, or a preformed container portion with ribs such that the drape is prevented from being drawn beneath the dislodgement mechanism, thereby enabling dislodgement of congealed sterile liquid from the drape.

Having described preferred embodiments of the new and improved surgical drape for use with surgical slush machines having an automatic dislodgement mechanism, it is believed that other modifications, variations and changes will be suggested to those skilled in the art in view of the teachings set forth herein. It is therefore to be understood that all such variations, modifications and changes are believed to tall within the scope of the present invention as defined by the appended claims.

What is claimed is:

1. In a thermal treatment system having a basin recessed in a top surface of a system housing for thermally treating a sterile medium and an automatic dislodgement mechanism disposed at the bottom of the basin for dislodging congealed sterile medium formed adjacent basin walls, said housing having a plurality of substantially vertical sides on which said top surface is supported, a surgical drape comprising:

a drape portion for covering said top surface and overhanging said housing sides;

a drape receptacle incorporated into said drape portion and configured to conform to, and be disposed within, said basin adjacent said dislodgement mechanism to contain said sterile medium within said basin; and securing means for selectively engaging the system housing and for preventing the drape from being pulled substantially further into the basin and thereby prevent the drape receptacle from being drawn beneath the dislodgement mechanism.

2. The drape of claim 1 wherein said securing means includes a skirt extending from said drape portion and having a plurality of locator bands to engage the system housing and secure the drape to the system;

wherein the skirt is of a precise length to enable placement of the drape receptacle in the basin without leaving any margin for excess portions of the drape to be drawn beneath the dislodgement mechanism.

3. The drape of claim 1 wherein said securing means includes a plurality of stirrups to selectively engage the system housing to secure the drape;

wherein each of the stirrups is of a precise length to enable placement of the drape receptacle in the basin without leaving any margin for excess portions of the drape to be drawn beneath the dislodgement mechanism.

4. The drape of claim 1 wherein said securing means includes a plurality of stirrups to selectively engage the system housing to secure the drape;

wherein each of said stirrups includes adjustable dimensions to enable placement of the drape receptacle in the basin without leaving any margin for excess portions of the drape to be drawn beneath the dislodgement mechanism.

5. The drape of claim 1 wherein said system includes a plurality of fasteners disposed on respective sides of said housing and said securing means includes a plurality of locator bands to engage corresponding ones of said plurality of fasteners to secure said drape to said housing.

6. The drape of claim 1 wherein said securing means includes a formed band for frictionally engaging the sides of said housing to secure the drape to the housing.

7. The drape of claim 6 wherein said formed band includes a plurality of stirrups to engage the system housing and secure the drape to the housing.

8. The drape of claim 1 wherein said system housing includes a plurality of posts disposed on said top surface, wherein each of said posts receive a corresponding cover and said securing means includes a plurality of openings for receiving said posts such that said covers maintain said posts through said openings to secure said drape to said housing.

9. The drape of claim 1 wherein said securing means includes positional fixing means for pressing portions of said drape against said basin walls to secure said drape to said housing.

10. The drape of claim 9 wherein said positional fixing means is removably disposed on said drape when said drape receptacle is placed in said basin.

11. The drape of claim 1 wherein said securing means includes an adhesive disposed on said drape to secure the drape to the system housing.

12. The drape of claim 11 wherein said adhesive includes double-sided adhesive tape.

13. The drape of claim 1 wherein said system housing includes adhesives disposed on said top surface and said securing means includes portions of said drape coincident said adhesives to engage said adhesives and secure the drape to the system housing.

14. A surgical drape for use in a thermal treatment system having a basin recessed in a top surface of a system housing for thermally treating a sterile medium, and an automatic dislodgement mechanism disposed at the bottom of the basin for dislodging congealed sterile medium from the drape adjacent basin walls, wherein said housing includes a plurality of substantially vertical sides on which said top surface is supported, said drape comprising:

a drape portion covering and hanging down from said top surface;

a preformed container portion fitted to match the contour of, and being disposed within, said basin adjacent said dislodgement mechanism, wherein said preformed container portion includes ribs disposed in the walls of said container portion; and securing means extending from said drape portion to hang down from said top surface and to selectively secure the drape to the system housing;

wherein said ribs disposed in said container portion walls are configured to allow air to flow along said basin beneath said container portion to prevent said container portion from being drawn by suction against the basin and beneath said dislodgement mechanism.

15. The drape of claim 14 wherein said securing means includes a formed band frictionally engaging the sides of the housing to secure the drape to the system.

16. A surgical drape for use in a thermal treatment system having a basin recessed in a top surface of a system housing for thermally treating a sterile medium, and an automatic dislodgement mechanism disposed at the bottom of the basin for dislodging congealed sterile medium from the drape adjacent basin walls, said drape comprising:

a drape portion for covering and hanging down from said top surface with a part of said drape portion conforming to, and being disposed within, said basin adjacent said dislodgement mechanism to form a drape receptacle;

wherein said drape is constructed of material having a coefficient of friction in the range of approximately 0.4–1.0 as measured against steel per ASTM 1983 to enable said drape to generate frictional forces with said basin sufficient to prevent said drape from being pulled substantially further into the basin beneath said dislodgement mechanism.

17. A surgical drape for use in a thermal treatment system having a basin recessed in a top surface of a system housing for thermally treating a sterile medium, and an automatic dislodgement mechanism disposed at the bottom of the basin for dislodging congealed sterile medium from the drape adjacent basin walls, said drape comprising:

a drape portion for covering and hanging down from said top surface with a part of said drape portion conforming to, and being disposed within, said basin adjacent said dislodgement mechanism to form a drape receptacle;

wherein said drape is formed of a metalocine-based olefin film having a flexibility approximately in the range of 10K–12K psi secant modulus measured by ASTM D882 to facilitate formation of air channels between said drape and basin when forming said drape receptacle;

wherein said air channels are configured to enable air to flow beneath said drape receptacle to prevent said drape from being drawn beneath said dislodgement mechanism by suction generated from dislodgement mechanism motion.

18. In a thermal treatment system having a basin recessed in a top surface of a system housing for thermally treating a sterile medium, a drape including a drape portion for covering and hanging down from said top surface with a part of said drape portion conforming to, and being disposed within, said basin to form a drape receptacle and a dislodgement mechanism disposed at the bottom of the basin for dislodging congealed sterile medium from the drape adjacent walls of the basin, a device for securing the drape to the housing to enhance dislodgement of the congealed medium, said device including positional fixing means for placement in the drape receptacle to press portions of said drape coincident said positional fixing means against the basin walls to secure the drape to the housing to prevent the drape from being pulled substantially further into the basin and thereby prevent said drape receptacle from being drawn beneath the dislodgement mechanism.

19. In a thermal treatment system having a basin recessed in a top surface of a system housing for thermally treating a sterile medium, a drape for maintaining sterility of said sterile medium, and a dislodgement mechanism disposed at the bottom of the basin for dislodging congealed sterile medium from the drape adjacent walls of the basin, wherein said housing includes a plurality of substantially vertical sides on which said top surface is supported, a method for enhancing dislodgement of the congealed medium comprising the steps of:

(a) forming said drape with a drape portion configured to cover and hang down from said top surface with a part of said drape portion conforming to and disposed within said basin adjacent said dislodgement mechanism to form a drape receptacle; and (b) further forming said drape with securing means to secure the drape to the system housing to prevent the drape from being pulled substantially further into the basin and thereby prevent the drape receptacle from being drawn beneath the dislodgement mechanism.

20. The method of claim 19 wherein step (b) further includes:

(b.1) forming said securing means to include a skirt extending from said drape portion and having a plurality of locator bands adapted to engage the system housing and thereby positionally secure the drape;

wherein the skirt is of a precise length to enable formation and placement of the drape receptacle in the basin without leaving any margin for excess portions of the drape to be drawn beneath the dislodgement mechanism.

21. The method of claim 19 wherein step (b) further includes:

(b.1) forming said securing means to have a plurality of stirrups adapted to engage the system housing to secure the drape;

wherein each of the plurality of stirrups is of a precise length to enable formation and placement of the drape receptacle in the basin without leaving any margin for excess portions of the drape to be drawn beneath the dislodgement mechanism.

22. The method of claim 19 wherein step (b) further includes:
(b.1) forming said securing means to have a plurality of stirrups adapted to engage the system housing to secure the drape;
wherein each of the plurality of stirrups includes adjustable dimensions to enable formation and placement of the drape receptacle in the basin without leaving any margin for excess portions of the drape to be drawn beneath the dislodgement mechanism.

23. The method of claim 19 wherein said system includes a plurality of fasteners disposed on respective sides of said housing and step (b) further includes:
(b.1) forming said securing means to have a plurality of locator bands to engage corresponding ones of said plurality of fasteners to secure said drape to said housing.

24. The method of claim 19 wherein step (b) further includes:
(b.1) forming said securing means to include a formed band to frictionally engage the sides of said housing and secure the drape to the housing.

25. The method of claim 24 wherein step (b.1) further includes:
(b.1.1) forming said formed band to include a plurality of stirrups adapted to engage the system housing and secure the drape to the housing.

26. The method of claim 19 wherein said system housing includes a plurality of posts disposed on said top surface, wherein each of said posts receive a corresponding cover and step (b) further includes the step of:
(b.1) forming said securing means to include a plurality of openings for receiving said posts such that said covers maintain said posts through said openings to secure said drape to said housing.

27. The method of claim 19 wherein step (b) further includes:
(b.1) forming said securing means to include positional fixing means for pressing portions of said drape against said basin walls to secure said drape to said housing.

28. The method of claim 27 wherein step (b1) further includes:
(b.1.1) forming said securing means such that said positional fixing means is removably disposed on said drape when said drape is placed in said basin to form said drape receptacle.

29. The method of claim 19 wherein step (b) further includes:
(b.1) forming said securing means to include an adhesive disposed on said drape to secure said drape to said housing.

30. The method of claim 29 wherein step (b.1) further includes:
(b.1.1) forming said adhesive to include double-sided adhesive tape disposed on said drape to secure said drape to said housing.

31. The method of claim 19 wherein said system housing includes adhesives disposed on said top surface and step (b) further includes:
(b.1) forming said securing means to include portions of said drape coincident said adhesives to engage said adhesives and secure the drape to the system housing.

32. In a thermal treatment system having a basin recessed in a top surface of a system housing for thermally treating a sterile medium, a drape for maintaining sterility of said sterile medium, and a dislodgement mechanism disposed at the bottom of the basin for dislodging congealed sterile medium from the drape adjacent walls of the basin, wherein said housing includes a plurality of substantially vertical sides on which said top surface is supported, a method for enhancing dislodgement of the congealed medium comprising the steps of:
(a) forming said drape to have a drape portion adapted to cover and hanging down from said top surface;
(b) defining in said drape a preformed container portion fitted to match the contour of, and adapted to be disposed within, said basin adjacent said dislodgement mechanism;
(c) forming ribs in the walls of said container portion; and
(d) disposing securing means on edges of said drape portion hanging down from said top surface for securing the drape to the system housing;
said ribs being configured to allow air to flow along said basin beneath said container portion to prevent said container portion from being drawn by suction against said basin and beneath said dislodgement mechanism.

33. The method of claim 32 wherein step (d) further includes:
(d.1) forming said securing means to include a formed band to frictionally engage the sides of the housing to secure the drape to the housing.

34. In a thermal treatment system having a basin recessed in a top surface of a system housing for thermally treating a sterile medium, a drape for maintaining sterility of said sterile medium, and a dislodgement mechanism disposed at the bottom of the basin for dislodging congealed sterile medium from the drape adjacent walls of the basin, a method for enhancing dislodgement of the congealed medium comprising the step of:
(a) forming said drape to have a drape portion for covering and hanging down from said top surface with a part of said drape portion conforming to, and being disposed within, said basin adjacent said dislodgement mechanism to form a drape receptacle, said drape being formed of a material having a coefficient of friction in the range of approximately 0.4–1.0 as measured against steel per ASTM 1983 to enable said drape to generate frictional forces with said basin sufficient to prevent said drape from being pulled substantially further into the basin beneath said dislodgement mechanism.

35. In a thermal treatment system having a basin recessed in a top surface of a system housing for thermally treating a sterile medium, a drape for maintaining sterility of said sterile medium, and a dislodgement mechanism disposed at the bottom of the basin for dislodging congealed sterile medium from the drape adjacent walls of the basin, a method for enhancing dislodgement of the congealed medium comprising the step of:
(a) forming said drape to have a drape portion for covering and hanging down from said top surface with a part of said drape portion conforming to, and being disposed within, said basin adjacent said dislodgement mechanism to form a drape receptacle, said drape being formed of a metalocine-based olefin film having a flexibility in the approximate range of 10K–12K psi secant modulus measured by ASTM D882 to facilitate formation of air channels between said drape and basin when forming said drape receptacle;
wherein said air channels are formed to enable air to flow beneath said drape receptacle to prevent said drape from being drawn beneath said dislodgement mechanism by suction generated from dislodgement mechanism motion.

36. In a thermal treatment system having a basin recessed in a top surface of a system housing for thermally treating a sterile medium, a drape having a drape portion for covering and hanging down from said top surface and being disposed within said basin to form a drape receptacle, and a dislodgement mechanism disposed at the bottom of the basin for dislodging congealed sterile medium from the drape adjacent walls of the basin, wherein said housing includes a plurality of substantially vertical sides on which said top surface is supported and said drape further includes securing means for securing the drape to the system housing, a method for enhancing dislodgement of the congealed medium comprising the step of:

(a) securing the drape to the housing via said securing means to prevent the drape from being pulled substantially further into the basin and thereby prevent the drape receptacle from being drawn beneath the dislodgement mechanism.

37. The method of claim 36 wherein said securing means includes a skirt extending from said drape portion and having a plurality of locator bands, and step (a) further includes:

(a.1) securing the drape to the housing by engaging said housing via said plurality of locator bands wherein the skirt is of a precise length to enable formation and placement of the drape receptacle in the basin without leaving any margin for excess portions of the drape to be drawn beneath the dislodgement mechanism.

38. The method of claim 36 wherein said securing means includes a plurality of stirrups and step (a) further includes:

(a.1) securing the drape to the housing by engaging the housing via said plurality of stirrups wherein each of the plurality of stirrups is of a precise length to enable formation and placement of the drape receptacle in the basin without leaving any margin for excess portions of the drape to be drawn beneath the dislodgement mechanism.

39. The method of claim 38 wherein each of said plurality of stirrups is adjustable and step (a.1) further includes:

(a.1.1) adjusting the length of each of said plurality of stirrups to secure said drape to said housing to enable formation and placement of the drape receptacle in the basin without leaving any margin for excess portions of the drape to be drawn beneath the dislodgement mechanism.

40. The method of claim 36 wherein said system includes a plurality of fasteners disposed on respective sides of said housing and said securing means includes a shortened skirt having a plurality of locator bands, and step (a) further includes:

(a.1) securing said drape to said housing by engaging said plurality of fasteners via corresponding ones of said plurality of locator bands.

41. The method of claim 36 wherein said securing means includes a formed band and step (a) further includes:

(a.1) securing the drape to the housing by sliding said drape over said housing such that said formed band frictionally engages the sides of said housing.

42. The method of claim 41 wherein said formed band includes a plurality of stirrups and step (a.1) further includes:

(a.1.1) securing said drape to said housing by engaging the system housing via said plurality of stirrups.

43. The method of claim 36 wherein said housing includes a plurality of posts disposed on said top surface, wherein each of said posts receive a corresponding cover, wherein said securing means includes a plurality of openings, and step (a) further includes:

(a.1) securing said drape by engaging said posts with said openings and fastening said covers on said posts to maintain said posts through said openings.

44. The method of claim 36 wherein said securing means includes fixings means for fixings said drape in said basin, and step (a) further includes:

(a.1) securing said drape by disposing said fixing means in said drape receptacle to press portions of said drape coincident said fixing means against said basin walls.

45. The method of claim 44 wherein said fixing means detachably interfaces said drape, and step (a.1) further includes:

(a.1.1) securing said drape by removably disposing said fixing means in said drape receptacle to press portions of said drape coincident said fixing means against said basin walls.

46. The method of claim 36 wherein said securing means includes adhesives, and step (a) further includes:

(a.1) disposing said adhesives on said drape; and (a.2) securing said drape by pressing portions of said drape coincident said adhesives against said top surface to enable said adhesives to adhere to the housing.

47. The method of claim 46 wherein said adhesives include double-sided adhesive tape, and step (a.1) further includes:

(a.1.1) disposing said double-sided adhesive tape on said drape; and step (a.2) further includes:

(a.2.1) securing said drape by pressing portions of said drape coincident said double-sided adhesive tape against said top surface to enable said tape to adhere to the housing.

48. The method of claim 36 wherein said system housing includes adhesives disposed on said top surface, wherein said securing means includes portions of said drape coincident said adhesives, and step (a) further includes:

(a.1) securing said drape by pressing said portions of said drape coincident said adhesives against said adhesives to enable said adhesives to adhere to the drape.

49. In a thermal treatment system having a basin recessed in a top surface of a system housing for thermally treating a sterile medium, a drape having a drape portion covering and hanging down from said top surface, a preformed container portion fitted to match the contour of, and being disposed within, said basin including ribs disposed in the walls of said container portion, securing means extending from said drape portion hanging down from said top surface for securing the drape to the system housing, and a dislodgement mechanism disposed at the bottom of the basin for dislodging congealed sterile medium from the drape adjacent walls of the basin, wherein said housing includes a plurality of substantially vertical sides on which said top surface is supported, a method for enhancing dislodgement of the congealed medium comprising the steps of:

(a) securing the drape to the system via said securing means; and (b) maintaining parts of said container portion away from walls of said basin via said ribs to enable air to flow between the container portion and dislodgement mechanism to prevent the container portion from being drawn beneath the dislodgement mechanism.

50. The method of claim 49 wherein said securing means includes a formed band and step (a) further includes:

(a.1) securing the drape to the housing by sliding the drape over the housing such that said formed band frictionally engages the sides of the housing.

* * * * *